United States Patent [19]
Lewis

[11] Patent Number: 5,947,986
[45] Date of Patent: Sep. 7, 1999

[54] HYGIENIC APPLICATOR

[76] Inventor: Darrin R. Lewis, 16205 Prairie, Detroit, Mich. 48221

[21] Appl. No.: 09/099,138

[22] Filed: Jun. 18, 1998

Related U.S. Application Data

[60] Provisional application No. 60/053,052, Jul. 21, 1997.

[51] Int. Cl.⁶ ................................. A61B 17/24
[52] U.S. Cl. .................. 606/161; 606/160; 606/162; 604/1; 604/2; 604/3
[58] Field of Search .................... 606/160, 161, 606/162; 604/1, 2, 3; 206/262, 205; 211/69; 422/310

[56] References Cited

U.S. PATENT DOCUMENTS

| D. 293,378 | 12/1987 | Alkire . |  |
|---|---|---|---|
| 1,221,231 | 4/1917 | Sharp | 604/3 |
| 3,626,946 | 12/1971 | Messey . |  |
| 4,446,965 | 5/1984 | Montiel | 206/205 |
| 4,767,398 | 8/1988 | Blasius . |  |
| 4,820,259 | 4/1989 | Stevens . |  |
| 4,863,422 | 9/1989 | Stanley . |  |
| 4,943,274 | 7/1990 | Edwards . |  |
| 5,016,651 | 5/1991 | Stalcup et al. | 604/1 |
| 5,209,757 | 5/1993 | Krug et al. . |  |
| 5,374,276 | 12/1994 | Lay . |  |
| 5,704,906 | 1/1998 | Fox | 604/1 |
| 5,846,215 | 12/1998 | Zygmont | 604/1 |

FOREIGN PATENT DOCUMENTS

| 580729 | 7/1933 | Germany . |
| PCT/IT90/ 00024 | 8/1991 | WIPO . |

*Primary Examiner*—Michael Buiz
*Assistant Examiner*—Lien Ngo
*Attorney, Agent, or Firm*—Richard C. Litman

[57] ABSTRACT

A hygienic applicator having a combination of moist and/or dry swab end sections made of absorbent material. The moist end section is pre-moistened with baby oil, cleaning solution, medicant, or any desired liquid. The dry end section can also be moistened with a preferred liquid and then dried, leaving this section impregnated with a desired residue. The end sections can be encapsulated with an easily removable wrap to prevent contamination. The wrap can be moisture-impermeable to retain the moisture of the wetted end sections. Wraps are incorporated for quickly unravelling the end sections just prior to use.

16 Claims, 3 Drawing Sheets

HYGIENIC APPLICATOR

CROSS-REFERENCE TO RELATED APPLICATION

This application claims the benefit of U.S. Provisional patent application Ser. No. 60/053,052, filed Jul. 21, 1997.

BACKGROUND OF THE INVENTION

1. Field of the Invention

The present invention relates to swab applicators and, more specifically, to a hygienic applicator having a combination of moist and/or dry sections, wherein the moist section does not lose moisture to the environment prior to use.

2. Description of Related Art

Various swab applicators have been developed in the past. Prior applicators were used to generally clean the ear, to remove the buildup of wax, dirt, and anything else that contributes to the discomfort of the ear. Some prior applicators are wetted with a cleaning agent. The disadvantage of this type of applicator is that, in order to be effective, the applied surfaces of the ear has to be generally dry, to avoid excessive dilution in wet environments. Prior art does not disclose an effective means for retaining the moisture in the moistened swab end sections.

There exist clear advantages for an applicator having both moist and dry sections. For example, when the ear canal is wet, perhaps after a shower, it is highly desirable to remove the excess moisture by using a dry applicator. But if the ear canal is dry, but one senses a blockage of wax or some foreign body, it is highly discomforting to insert a dry applicator into the ear canal. This dry-on-dry contact can be painful to the highly sensitive ear canal due to excessive friction. Conversely, when the ear canal is wet, it is highly undesirable to use a wet applicator for cleaning since it will be ineffective in highly moist environments. A purely dry applicator will only absorb moisture in a wet environment. In order for all the benefits of a moist and dry applicator to be fulfilled, it is essential that a means for retaining moisture in the moistened end sections, prior to use, be invented.

Accordingly, a need will be seen for a hygienic applicator device that can provide a convenient wet tip and a separate dry tip. The user could then have the option of selecting the tip that is most preferable at the time of usage. The user can rotate between the wet and dry tips to create a customized condition. In addition, it would be highly desirable if the dry applicator can contribute a desired liquid, such as soap solution, cleaning solution, baby wipe solution, baby oil, mineral oil, medicant, etc., to a wet environment since this would bypass the step of first drying the ear and then applying a wet applicator having the desired solution. Further, there is a need for a device as described above that is easily and economically produced, without complicated chemical or mechanical means for producing moist or dry conditions in the applicator, and more importantly, safe to the user.

U.S. Design Pat. No. 293,378 issued to Alkire on Dec. 22, 1987 describes an ear cleaner having an elongated section and a tilted portion. A spherical applicator is attached on the end portion of the tilted portion. At the end of the straight portion, there is a probe or scoop-like device. This device can be very dangerous since inserting any solid probe into the ear canal can cause permanent damage. Further, this patent does not teach or suggest any means for retaining moisture in the end pieces prior to use.

U.S. Pat. No. 3,626,946 issued to Messey on Dec. 14, 1971 describes another ear cleaner. It discloses a device that includes a non-woven fabric twisted and pressed about a cigar-shaped mandrel to form a member that can be inserted into the human ear. The device has no hard points that could damage the ear canal. The device has only one applicator end portion. This patent does not teach or suggest any means for retaining moisture in the end pieces prior to use.

U.S. Pat. No. 4,767,398 issued to Blasius on Aug. 30, 1988, describes a swab applicator with the swab made of a fibrous, non-woven material having an outer flock surface. This device is useful in the application of cosmetics such as eye shadow and eye liner. This patent does not teach or suggest any means for retaining moisture in the end pieces prior to use.

U.S. Pat. No. 4,820,259 issued to Stevens on Apr. 11, 1989 describes a device for cleaning the external ear. The device discloses end pieces that have a cleaning agent, such as soap incorporated therein. This device cannot be inserted into the ear canal. This patent does not teach or suggest any means for retaining moisture in the end pieces prior to use.

U.S. Pat. No. 4,863,422 issued to Stanley on Sep. 5, 1989 describes a double-ended compressible tubular swab applicator comprising a length of tubular material (in the shaft) containing heat generating chemical means for delivering heat treating liquid. Medicament is encapsulated in a plastic tube, surrounded by a heat generating chemical. Upon sufficient pressurization, an exothermic reaction proceeds and hot medicament flows into the end portions of the applicator. Once the reaction proceeds, it cannot be controlled. Exothermic reactants placed in swab applicators must be handled with extreme caution.

U.S. Pat. No. 4,943,274 to Edwards on Jul. 24, 1990, describes an apparatus for insertion through an aperture in an earlobe after an ear piercing, to deliver medicament to the punctured areas of the ear lobe. The device includes a squeezable reservoir portion at one end and a medicated felt pad on the opposite end. The medicant is released by squeezing the reservoir and flows out of various conduits. The felt pad serves to medicate the interior side of the earlobe adjacent the aperture and to receive excess medicament. This device is exclusively a wet applicator. This patent does not teach or suggest means for economically retaining moisture in the end piece prior to use.

U.S. Pat. No. 5,209,757 issued to Krug et al. on May 11, 1993 describes an illuminated ear cleaning device with the illuminating means in close proximity to an ear cleaning means. This patent does not teach or suggest any means for retaining moisture in the end pieces prior to use.

U.S. Pat. No. 5,374,276 issued to Lay on Dec. 20, 1994 describes an ear wax remover. This device comprises an elongate rod having an extractor head on a first end and a swab attachment portion on a second end. The extractor head is comprised of a mushroom shaped tip. This patent does not teach or suggest any means for retaining moisture in the end pieces prior to use.

German Patent Number 580 729 published on Jul. 15, 1933, of Hollstein describes conical swabs at opposite ends of an applicator device. It is believed that this patent does not teach or suggest any means for retaining moisture in the end pieces prior to use. It is further believed that this device does not teach or suggest any form of wet and dry hygienic applicators for cleaning the ear canal.

PCT application number PCT/IT90/00024 published on Aug. 22, 1991 of Segreto describes a device for removal of wax from the auditory meatus that generates suction in the ear canal to remove excess wax buildup. This is achieved by igniting one end of the device while the other end of the device is spaced inside the ear canal. This device does not teach or suggest any form of wet and dry hygienic applicators for cleaning the ear canal. Further, this patent does not teach or suggest any means for retaining moisture in the end pieces prior to use.

None of the above noted inventions and patents, taken either singly or in combination, is seen to describe the instant invention as claimed.

SUMMARY OF THE INVENTION

The a hygienic applicator according to the invention has a combination of moist and/or dry swab end sections made of absorbent material. The moist end section is pre-moistened with a desired liquid, such as soap solution, cleaning solution, baby wipe solution, baby oil, mineral oil, medicant, and the like. The dry end section can also be moistened with a preferred liquid and then dried, leaving this section impregnated with a desired residue. The end sections can be encapsulated with an easily removable wrap to prevent contamination. The wrap can be moisture-impermeable to retain the moisture of the wetted end sections. Means for fastening the wraps onto the end sections are incorporated, in addition to means for quickly unravelling the end sections just prior to use.

Accordingly, it is a principal object of the present invention to provide a hygienic applicator which can be used to effectively clean the ear canal, external ear, or any other external skin surface in both wet and dry environmental conditions.

Another of the objects of the present invention is to provide a hygienic applicator in which the moist end portion of the applicator is moistened with a desired liquid, such as soap solution, cleaning solution, baby wipe solution, baby oil, mineral oil, medicant and the like.

Yet another of the objects of the present invention is to provide a hygienic applicator in which the dry swab applicator is first saturated with a desired liquid, and then dried to extricate some or all the moisture, such that when the dry swab applicator is placed in a wet environment, such as a wet ear canal, the dry applicator is then re-moistened to reconstitute the desired mineral oil, cleaning agent, and the like.

Still another of the objects of the present invention is to provide a hygienic applicator in which the end sections are wrapped in a moisture-impermeable wrap to prevent contamination and evaporation of moisture from the moistened end sections.

A further object of the present invention is to provide a hygienic applicator which is economical to produce.

A final object of the present invention is to provide a dispenser for use with non-wrapped moist and dry applicators.

These and other objects of the present invention will be more readily apparent as the nature of the invention is hereinafter more fully described, illustrated and claimed with reference being made to the attached drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is a hygienic applicator having moist and/or dry swab end sections. The end sections may be covered by wrappers to prevent contamination. The wrappers may be moisture impermeable to prevent the moistened end sections from drying out prior to use.

Embodiments of the various aspects of the present invention will now be explained with reference to the accompanying drawings. By way of illustration and not limitation, FIGS. 1 to 5 are presented to show the preferred embodiments of the applicant's invention.

Figure 3:
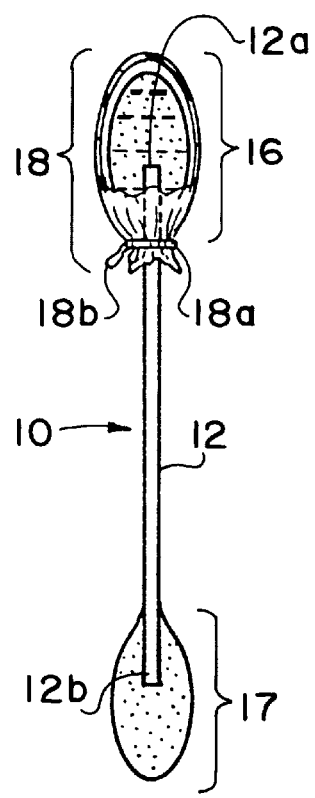
FIG. 3 is a longitudinal cross-sectional view of a hygienic applicator with one of the swab end sections moistened with a desired liquid and wrapped in an easy-to-remove moisture-impermeable wrapper.

In one preferred embodiment, the hygienic applicator 10 in FIG. 3 comprises a shaft 12 with two end portions 12a, 12b. It is preferred that the shaft 12 is made of a substantially moisture impermeable material such as plastic. A substantially water impermeable paper-based shaft 12 is also preferred. A moisture-absorbent first and second end piece 16, 17 is attached to each of the end portions 12a, 12b of the shaft 12. Preferably, the moisture-absorbent end pieces 16, 17 are made of sterile soft cotton. The first end piece 16 is moistened with any desired liquid. Preferably, the desired liquid includes soap solution, cleaning solution, baby wipe solution, baby oil, mineral oil, medicant and the like. The second end piece 17, in this embodiment, is dry.

A wrap 18 encapsulates the first end piece 16. The dry second end piece 17 may also be covered by a wrap 18. The wrap 18 is preferably made of a moisture-impermeable material, to prevent the loss of moisture from the pre-moistened end piece prior to use. Additionally, the wrap 18 acts to prevent moisture from the environment from entering the first and second end pieces 16, 17. (In FIG. 3, the end section 17 is shown without a wrap 18). The wrap 18 also serves to prevent contamination of the end pieces 16, 17 by the environment. Highly humid conditions encourage the growth of fungus, mildew and microorganisms.

To prevent the wrap 18 from unravelling, a securing means in the form of a strap 18a tightly secures the wrap 18 around the shaft 12. It is preferred that the strap 18a is a flexible, longitudinal band that is made of either a paper or plastic material, held together by an adhesive. It is preferred that the adhesive is relatively weak, so that the strap 18a can be broken easily, enabling the easy unravelling of the wrap 18, prior to use. The strap 18a includes a quick release handle portion 18b that is part of the strap 18. The quick release handle is pulled, prior to use, to break the strap, to permit the unravelling of the wrap 18. It is preferred that the wrap 18 is made of a substantially moisture impermeable material such as cellophane, aluminum foil, or plastic.

It is highly advantageous to have, both moist and dry end pieces 16, 17. The user can control the level of moisture to the applied surface by rotating between the application of the moist end piece 16 and the dry end piece 17. For example, if the user seeks to clean the ear canal (after a shower), the user would insert the clean, dry end piece 17 to remove excess moisture, followed by the moist end piece 16. Conversely, if the ear canal is dry, the user may want to insert the moist end piece 16, containing a mild cleaning solution, e.g. dilute soap solution, and then dry the ear canal with the dry end piece 17.

In addition, the applicator 10 can be useful in treating minor cuts and the like. If the liquid in the moistened end portion 16 is a medicament, e.g. iodine, the moistened end portion 16 can be applied to a cut and excess fluid can be wiped by the clean, dry end piece 17.

The dry end piece 17 of FIG. 3 may be dipped in a desired liquid, preferably at the production site, and allowed to reach a desired state of dryness, before being wrapped by a moisture impermeable wrap (not shown). It is also foreseeable that atomized particles of desired liquid can be sprayed onto the end sections 16, 17.

There are advantages to having dry or partially dry residue from the desired liquid deposited on the dry end piece 17. For instance, the user may simply insert this type of dry end piece 17 directly into a wet ear canal. The preexisting moisture in the ear canal will moisturize the residue of the dry or substantially dry end piece 17, reconstituting the desired cleaning solution, baby oil, or the like. This process simultaneously cleans and dries the ear. This bypasses the usual step of first drying the wet ear canal with a dry end piece 17 so that the cleaning solution will not be overly diluted; followed by the use of a wet end piece 16 dipped in a desired liquid; and finally, the application of another dry end piece 17 to dry the ear canal.

Figure 4:
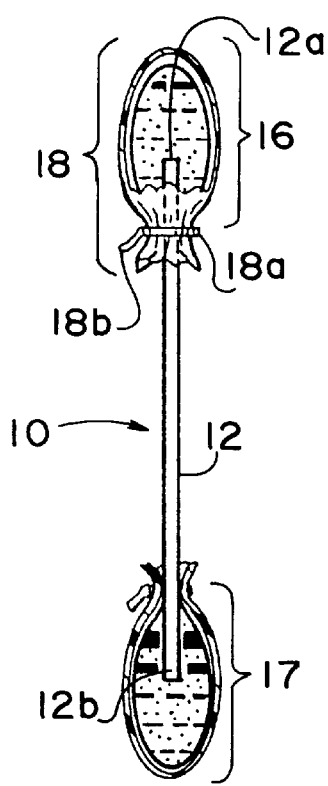
FIG. 4 is a longitudinal cross-sectional view of a different embodiment of the hygienic applicator with both of the swab end sections moistened, each with a desired liquid, wrapped in an easy-to-remove moisture impermeable wrapper.

Another embodiment of the applicator 10 is shown in FIG. 4. In this embodiment, both end pieces 16, 17 each contain desired liquids. The end pieces 16, 17 may contain the same or different liquids. In the case where the end pieces 16, 17 contain different liquids, it is preferred that different liquids in the end pieces 16, 17 are related in their usage. For example, one end piece 16 may contain alcohol, and the other end piece 17 may contain iodine. To treat a cut, the user would first apply the end piece 16 containing the alcohol to the surface of the cut to kill microorganisms and to generally clean the wound and surrounding areas. After the alcohol is allowed to dry, killing the microorganisms, the end piece 17 containing iodine can be applied to further disinfect the wound.

In yet another embodiment (not shown, but similar to FIG. 4), both end pieces 16, 17 are dry. Both end pieces 16, 17 are preferably encapsulated by wraps 18. It is preferred that the wraps 18 that are used in this embodiment are substantially moisture-impermeable to prevent outside moisture from entering the end pieces 16, 17, although material such as moisture-permeable paper can be used to wrap the end pieces 16, 17, to reduce the cost of manufacture.

Figure 1:
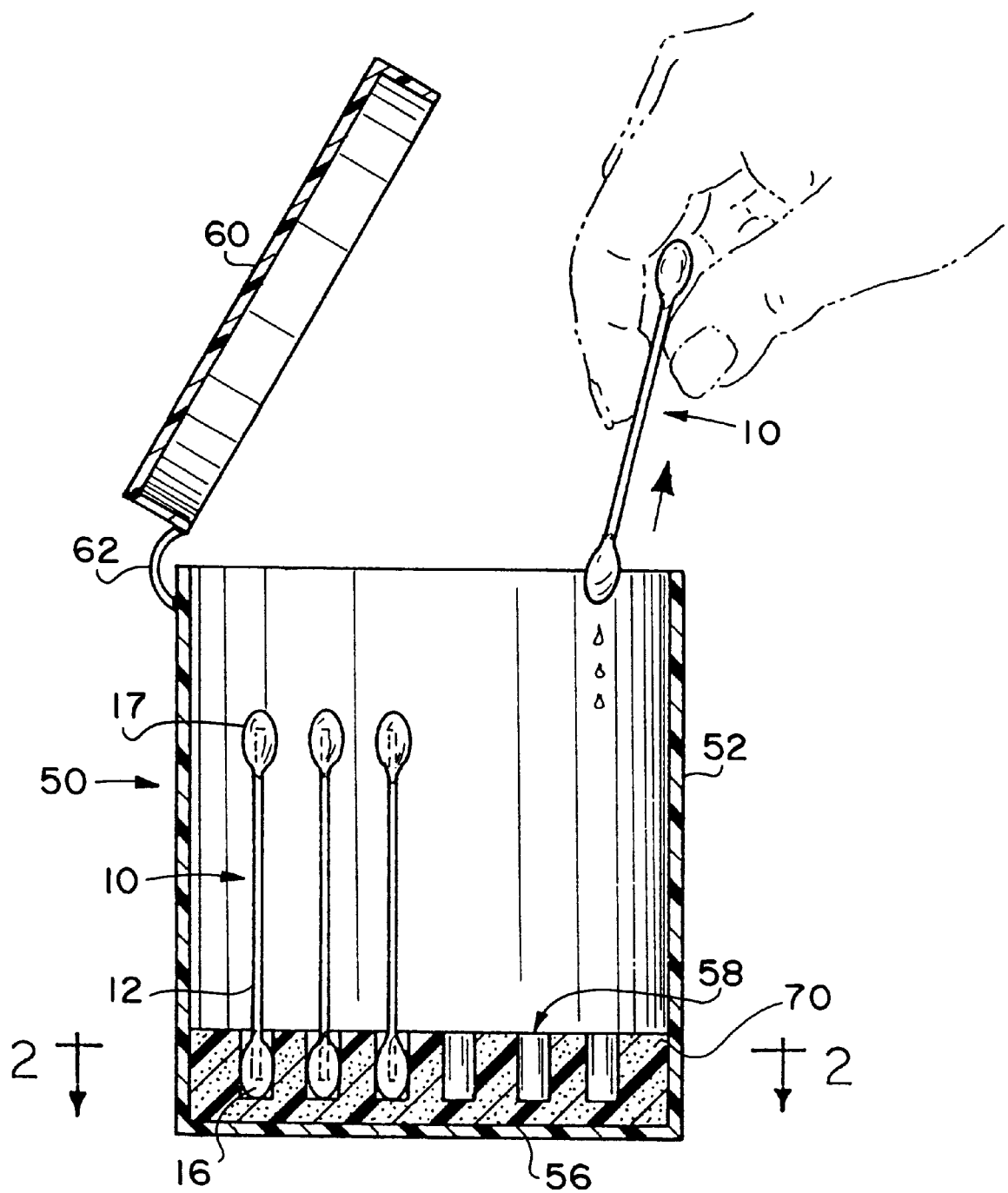
FIG. 1 is an environmental, cross-sectional view of a dispenser for hygienic applicators having some applicators shown inserted into moistened swab receptors of the dispenser.
Figure 2:
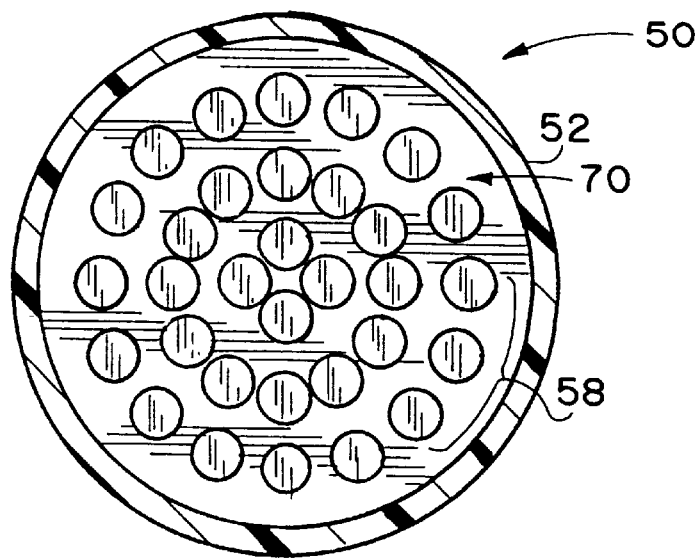
FIG. 2 is a sectional plan view of the dispenser for hygienic applicators along line 2—2 of FIG. 1.

In FIG. 1, a dispenser 50 is shown. Unlike the embodiments, thus presented, which require that the applicators 10 are filled with desired liquids and wrapped preferably at the site of manufacture, the dispenser 50 is shown for use with unwrapped applicators 10.

The dispenser 50 is preferably made out of material that will not easily react with the various liquids that may be used in conjunction with the applicators 10. Further, the dispenser 50 should be moisture-proof and hermetically sealable, to prevent loss of moisture from within the dispenser 50 to the outside environment and vice versa. It is preferred that the dispenser 50 is made out of non-reactive plastic.

The dispenser 50 for the hygienic applicators 10, in this embodiment, includes a cylindrical housing with a bottom wall 56 and sidewall 52. The side wall 52 surrounds the bottom wall 56 and extends vertically upward. A base 70, recessed above the bottom wall 56, contain a desired liquid. The base 70 includes a plurality of recessed cavitations 58 for receiving end portions 16 of the hygienic applicators 10. Liquid from the base 70 flows into the cavitations 58 to wet the end sections 16 of the applicators 10. It is preferred that the liquid-filled base 70 is made substantially of a liquid absorbing and releasing material, such as a partially perforated open celled foam, such as used for stamp pads, capable of absorbing and holding moisture. In one embodiment of the present invention, the liquid-filled base may be made of a sponge material.

If the shaft 12 of the applicator 10 is moisture-impermeable, the other end section 17 will remain substantially dry. To hermetically enclose this structure, a cover 60, preferably made of the same non-reactive material as the cylindrical housing of the dispenser 50, covers the side walls to hermetically seal the dispenser 50. Hinge device 62 allows the cover 60 to be quickly and easily opened and closed.

Figure 5:
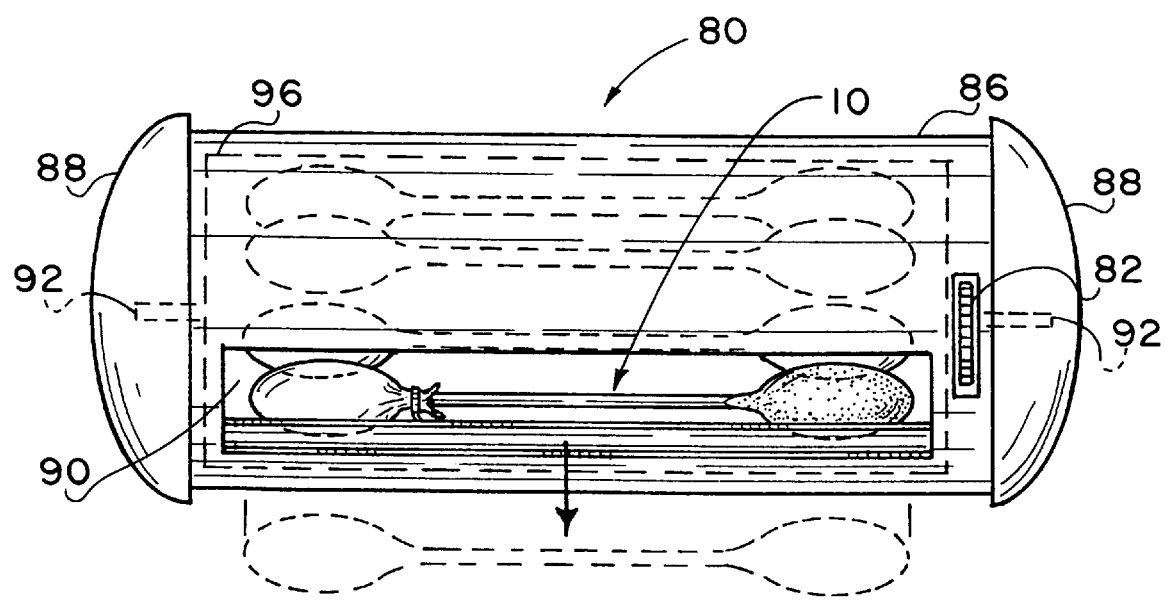
FIG. 5 is another embodiment of a dispenser with pre-wrapped hygienic applicators stored in thereof.

Another embodiment of a dispenser 80 is shown in FIG. 5. The dispenser 80 is a cylindrical design, having a cylindrical wall 86 that surrounds a plurality of applicators 10. The opposite end portions of the cylindrical wall 86 are enclosed by end walls 88. The cylindrical wall 86 has an opening 90 that permits the extrication of one applicator 10 each time the release mechanism 82 is activated. A rotative attachment 92 is holding a drum magazine 96 containing the applicators 10. Each time the release mechanism 82 is activated, the rotative attachment 92 rotates about its axis, releasing an applicator 10 through the opening 90.

It is to be understood that the present invention is not limited to the embodiments described above, but encompasses any and all embodiments within the scope of the following claims.

I claim:

1. A hygienic applicator comprising:
   a shaft;
   a moisture absorbent end piece attached to at least one end portion of said shaft;
   a wrap encapsulating said end piece to prevent contamination of said end piece; and
   securing means for preventing the unravelling of said wrap;
   wherein said shaft extends beyond said wrap at said securing means.

2. The hygienic applicator according to claim 1, wherein the securing means for preventing the unravelling of said wrap include a band that fastens said wrap around said shaft.

3. The hygienic applicator according to claim 2, wherein said band includes a quick release handle portion for easily breaking said band to unravel said wrap just prior to use.

4. The hygienic applicator according to claim 1, wherein said wrap is selected from a group consisting of cellophane, aluminum foil, paper, and plastic.

5. The hygienic applicator according to claim 1, wherein said shaft is made of a material selected from the group consisting of paper and plastic.

6. The hygienic applicator according to claim 1, wherein said moisture absorbent end piece being made from soft cotton material in the shape of an elliptical sphere.

7. A hygienic applicator comprising:
   a substantially moisture impermeable shaft;

a moisture absorbent end piece attached to at least one end portion of said shaft;

said end piece pre-moistened with a desired liquid;

a moisture-repellant wrap encapsulating said pre-moistened end piece to prevent premature drying of said pre-moistened end piece; and securing means for preventing the unravelling of said wrap;

wherein said shaft extends beyond said wrap at said securing means.

8. The hygienic applicator according to claim 7, wherein the securing means for preventing the unravelling of said wrap include a band that fastens said wrap around said shaft.

9. The hygienic applicator according to claim 8, wherein said band includes a quick release handle portion for easily breaking said band to unravel said wrap just prior to use.

10. The hygienic applicator according to claim 7, wherein said moisture absorbent end piece includes:

residue deposited on said end piece by moistening said end piece in a liquid and evaporating said end piece to a desired level of dryness.

11. The hygienic applicator according to claim 7 wherein the liquid for the moistened ends are selected from a group consisting of baby oil, baby wipe solution, mineral oil, soap solution, and medicant.

12. The hygienic applicator according to claim 7, wherein said wrap is substantially composed of a group consisting of cellophane, aluminum foil, moisture-impermeable paper, and plastic.

13. The hygienic applicator according to claim 7, wherein said shaft is made from a group consisting of paper and plastic.

14. The hygienic applicator according to claim 7, wherein said moisture absorbent end piece being made from soft cotton material in the shape of an elliptical sphere.

15. A dispenser for a hygienic applicator comprising:

a bottom wall;

side wall surrounding said bottom wall and extending vertically;

a liquid-filled base recessed above said bottom wall;

said base including a plurality of recessed cavitations for receiving end portions of the hygienic applicators;

a cover hermetically sealing the dispenser thereby retaining the moisture level within the dispenser; and hinge means for enabling the quick opening and closing of said cover;

wherein said liquid-filled base is made substantially of a liquid absorbing and releasing material filled with a desired liquid.

16. A dispenser for the hygienic applicator as in claim 15 wherein said liquid-filled base is made of a sponge material defining a plurality of perforations for insertion a swab.

* * * * *